(12) United States Patent
Frater et al.

(10) Patent No.: US 11,788,548 B2
(45) Date of Patent: Oct. 17, 2023

(54) QUIET BLOWER APPARATUS AND SYSTEM AND METHOD FOR REDUCING BLOWER NOISE

(71) Applicant: ResMed Pty Ltd, Bella Vista (AU)

(72) Inventors: Robert Henry Frater, Lindfield (AU); Hamish Alexander Urquhart, Dural (AU); Dmitri Anatolievich Doudkine, Chatswood (AU); Barton John Kenyon, Ashfield (AU)

(73) Assignee: ResMed Pty Ltd

( * ) Notice: Subject to any disclaimer, the term of this patent is extended or adjusted under 35 U.S.C. 154(b) by 778 days.

(21) Appl. No.: 16/517,182

(22) Filed: Jul. 19, 2019

(65) Prior Publication Data
US 2020/0018324 A1   Jan. 16, 2020

Related U.S. Application Data

(63) Continuation of application No. 14/198,220, filed on Mar. 5, 2014, now Pat. No. 10,393,142, which is a
(Continued)

(51) Int. Cl.
*F04D 29/42* (2006.01)
*F04D 29/66* (2006.01)
*A61M 16/00* (2006.01)

(52) U.S. Cl.
CPC ..... *F04D 29/4226* (2013.01); *A61M 16/0057* (2013.01); *A61M 16/0066* (2013.01); *A61M 16/0069* (2014.02); *F04D 29/663* (2013.01); *A61M 2205/3375* (2013.01); *A61M 2205/42* (2013.01); *Y10T 29/49243* (2015.01)

(58) Field of Classification Search
CPC .............. F04D 29/4226; F04D 29/663; A61M 16/0057; A61M 16/0066; A61M 16/0069; A61M 2205/3375; A61M 2205/42; Y10T 29/49243
See application file for complete search history.

(56) References Cited

U.S. PATENT DOCUMENTS

| | | |
|---|---|---|
| 4,944,310 A | 7/1990 | Sullivan |
| 5,299,916 A | 4/1994 | Schmid |

(Continued)

FOREIGN PATENT DOCUMENTS

| | | |
|---|---|---|
| DE | 728617 | 11/1942 |
| DE | 20022013232 U | 8/2002 |

(Continued)

OTHER PUBLICATIONS

International Search Report for corresponding International Application No. PCT/AU2006/001945 dated Feb. 19, 2007.
(Continued)

*Primary Examiner* — Elliot S Ruddie
(74) *Attorney, Agent, or Firm* — Botos Churchill IP Law LLP

(57) ABSTRACT

A blower assembly including a motor, an impeller and a volute that is configured such that an inlet chamber of the volute and an outlet chamber of the volute are divided from one another by an airtight membrane and the membrane is configured to allow the transmission of pressure waves between the inlet and outlet chambers.

21 Claims, 14 Drawing Sheets

Related U.S. Application Data continuation of application No. 13/679,375, filed on Nov. 16, 2012, now Pat. No. 8,702,379, which is a continuation of application No. 12/087,075, filed as application No. PCT/AU2006/001945 on Dec. 20, 2006, now Pat. No. 8,337,145.

(60) Provisional application No. 60/755,776, filed on Jan. 4, 2006.

(56) References Cited

U.S. PATENT DOCUMENTS

| | | | |
|---|---|---|---|
| 6,142,732 | A | 11/2000 | Chou et al. |
| 6,216,691 | B1 | 4/2001 | Kenyon et al. |
| 6,315,526 | B1 | 11/2001 | Jones |
| 6,474,960 | B1 * | 11/2002 | Hansmann ............ F04D 29/668 |
| | | | 415/206 |
| 6,622,724 | B1 | 9/2003 | Truitt et al. |
| 6,644,311 | B1 * | 11/2003 | Truitt ................. A61M 16/024 |
| | | | 128/204.22 |
| 6,910,483 | B2 | 6/2005 | Daly et al. |
| 6,988,057 | B2 | 1/2006 | Huang et al. |
| 7,762,373 | B2 | 7/2010 | Bolton et al. |
| 7,789,194 | B2 | 9/2010 | Lathrop et al. |
| 8,337,145 | B2 | 12/2012 | Frater et al. |
| 8,702,379 | B2 | 4/2014 | Frater et al. |
| 2003/0168064 | A1 * | 9/2003 | Daly ................. A61M 16/0816 |
| | | | 128/204.18 |
| 2005/0053487 | A1 | 3/2005 | Munker et al. |
| 2009/0007912 | A1 | 1/2009 | Lindell et al. |
| 2009/0301482 | A1 | 12/2009 | Burton |
| 2010/0290928 | A1 | 11/2010 | Jung et al. |

FOREIGN PATENT DOCUMENTS

| | | | |
|---|---|---|---|
| FR | 2843305 | A1 | 2/2004 |
| FR | 2866812 | A1 | 9/2005 |
| JP | 2006207508 | A | 8/2006 |
| WO | 1980001501 | A1 | 7/1980 |
| WO | 2000038771 | A1 | 7/2000 |
| WO | 2005097244 | A1 | 10/2005 |
| WO | WO-2005097244 | A1 * | 10/2005 ............ A61M 16/10 |

OTHER PUBLICATIONS

European Search Report dated Nov. 28, 2012 for EP 06828049.
Julien RM "Chapter 2: Pharmacodynamics: How Drugs Act". A Primer of Drug Action (9th Edition). Worth Publishers, 2001, 33-57.
Osci A. [Editor] "Chapter 27: Structure-Activity Relationship and Drug Design", Remington's Pharmaceutical Sciences (16th Edition), Mack Publishing, 1980, pp. 420-435.

* cited by examiner

QUIET BLOWER APPARATUS AND SYSTEM AND METHOD FOR REDUCING BLOWER NOISE

CROSS-REFERENCE TO RELATED APPLICATIONS

This application is a continuation of U.S. patent application Ser. No. 14/198,220, filed on Mar. 5, 2014 which is a continuation of U.S. patent application Ser. No. 13/679,375, filed Nov. 16, 2012, now U.S. Pat. No. 8,702,379, which is a continuation of U.S. patent application Ser. No. 12/087,075, filed Jul. 21, 2009, now U.S. Pat. No. 8,337,145, which is a national phase entry under 35 U.S.C. § 371 of International Application No. PCT/AU2006/001945 filed Dec. 20, 2006, which claims priority from U.S. Provisional Patent Application No. 60/755,776 filed Jan. 4, 2006, all of which are incorporated herein by reference.

FIELD OF THE INVENTION

The present invention relates generally to blower assemblies for use in respiratory treatment of patients. More specifically, the present invention relates to a quiet blower apparatus and a system and method for reducing blower noise.

BRIEF DESCRIPTION OF RELATED ART

Blower assemblies have conventionally been used in a variety of situations. In many of these situations, it is desirable for the blower to be quiet.

One such situation where a quiet blower is important is during the treatment of Obstructive Sleep Apnea (OSA) using Continuous Positive Airway Pressure (CPAP). CPAP technology was invented by Sullivan and is described in U.S. Pat. No. 4,944,310. During OSA treatment with CPAP, a supply of air or breathable gas at a positive pressure is created by a blower assembly and is delivered by an air delivery conduit to a patient interface, such as a nasal mask. Since this method of treatment is generally administered while a patient is sleeping, it is important that the blower operates quietly so as not to disturb the patient.

Generally, the blower is a dynamic pump that includes an electric motor, an impeller, and a volute. The volute is a housing that surrounds the impeller and has an inlet and an outlet. The electronic motor spins the impeller which imparts rotational motion to the air. A pressure develops inside the volute as a result of a restriction at the outlet of the volute.

Treatment of OSA using CPAP has been successful but reduction of noise during treatment has been a continuing challenge. Such reduced nose is also desirable in other applications of blowers such as air-conditioning units, hydraulic pumps and other such apparatus. Some of the noise produced by the blower can be reduced by mechanically isolating the blower. Specifically, by mounting the blower on springs or a rubber block inside a heavy and stiff enclosure, some of the blower noise can by mechanically isolated. However, the prior art methods have only been marginally successful and they make the device (such as the CPAP device) large and heavy when, in fact, portability and a smaller size is often desirable.

Other applications where the present invention can be useful is in computers and other apparatus where a blower is used to cool electrical circuits as a lot of these apparatus are used in quiet places. Other possible applications include other types of medical devices and the like.

Methods of blower noise reduction using mufflers and other in-line filter mechanisms have also been tried. However, small mufflers and in line filters are generally not effective at reducing relatively low frequency noise and require a certain size to accomplish better noise reduction. In contrast, the membrane system is not primarily an in-line filter but is a mechanism for providing noise reduction by interference of the inlet and outlet noise. Thus, the size of the interfering system is not restricted by resonance effects linked to a filter design. It will be beneficial to use this membrane system in conjunction with other filter elements, particularly where the filter elements are designed to reduce high frequency noise beyond the frequencies where the membrane system is effective. It will be seen that provided the acoustic path lengths from the inlet and outlet are similar, means for high frequency filtering may be included in both the inlet and outlet path prior to effecting noise cancellation at relatively low frequencies with the membrane.

SUMMARY OF THE INVENTION

A first aspect of the invention is to provide a system for reducing noise in a blower or flow generator that exposes the acoustic components of the inlet and outlet of said blower to one another. Another aspect of the invention is to provide blower or flow generator apparatus having external inlet and outlet chambers in acoustic but not fluid communication with one another.

Another aspect of the invention is to provide an electric motor, impeller, volute and housing assembly having an inlet chamber and an outlet chamber divided by an air tight membrane that allows the transmission of pressure waves between the inlet and outlet chambers.

Another aspect of the invention is to provide blower noise reducing apparatus comprising means for the communication of sound pressure waves that are generally 180 degrees out-of-phase with one another.

Another aspect of the invention provides a means for combining sound waves which will result in a net reduction of acoustic noise across a determined frequency range.

According to another aspect of the present invention, a system is provided for reducing noise generated by a blower, the system comprising a blower, comprising a motor, an impeller, an inlet ort, and an outlet ort; an enclosure the enclosure being divided into an inlet section including an enclosure inlet port and an outlet section including an enclosure outlet port; and a flexible membrane configured to divide the enclosure into the inlet section and the outlet section.

In one embodiment, the blower is located in the enclosure.

In one embodiment, the flexible membrane is balloon like and is in fluid connection with the blower outlet port and the enclosure outlet port.

In one embodiment, the flexible membrane is donut-shaped and surrounds the blower and that is coupled to the enclosure outlet port.

In one embodiment, the area of the flexible membrane is substantially larger than the cross-sectional area of the blower outlet port.

In one embodiment, the blower is one used in treating obstructive sleep apnea.

In one embodiment, the blower is one used in treating obstructive sleep apnea with continuous positive airway pressure.

In one embodiment, the blower is part of a portable device, comprising the blower, a casing and a carrying handle According to another aspect of the present invention, a method for reducing noise generated by a blower is provided, the method comprising hosing at least an inlet port and outlet port of a blower in an enclosure which also includes an inlet section and an outlet section; dividing the enclosure into at least two sections with one or more flexible membranes; and configuring the one or more flexible membranes so that the blower inlet port and blower outlet port are acoustically coupled.

In one embodiment, the inlet section and outlet section are divided substantially by one membrane.

In another embodiment, the inlet and outlet section are divided by at least two membranes, separated by a layer of fluid medium able to transmit acoustic waves between the inlet and outlet sections.

In one embodiment, the flexible membrane is a balloon that is configured to couple the blower outlet port to the enclosure outlet port.

In one embodiment, the flexible membrane is a donut that surrounds the blower and that is coupled to the enclosure outlet port.

In one embodiment, the area of the flexible membrane is substantially larger that the cross-sectional area of the blower outlet port.

In one embodiment, the blower is one used in treating obstructive sleep apnea.

In one embodiment, the blower is one used in treating obstructive sleep apnea with continuous positive airway pressure.

In one embodiment, the blower is part of a portable device, comprising the blower, a casing and a carrying handle

BRIEF DESCRIPTION OF THE DRAWINGS

Additional features and advantages of the present invention will become apparent from the following detailed description of embodiments of the invention in conjunction with the accompanying drawings in which.

It should be noted that like reference numbers in these figures denote the same or similar features.

DETAILED DESCRIPTION OF EMBODIMENTS

The noise generated by a blower includes radiated noise and conducted noise. As discussed above, radiated noise can be reduced by mechanically isolating the blower by mounting the blower on springs inside a heavy and stiff enclosure.

In the device and system of the present invention this also a suitable way to reduce the radiated noise. Radiated noise radiates from both the blower apparatus generally, and the blower inlet.

Conducted noise travels along the mask conduit towards the patient and can be reduced by including inlet an outlet mufflers. Generally, by increasing the size of a muffler, the muffler will increase the amount of noise reduction. However, as discussed above, making the muffler large may conflict with the general commercial desirability of wanting to make the overall device small and unobtrusive, less expensive, and/or less complex.

In an embodiment, it is desirable that the sound be coherent sound such that it may be combined with another coherent sound to achieve at least partial cancellation. As the frequency of the sound leaving the blower increase, coherency decreases and therefore cancellation becomes more difficult and less effective.

Figure 1:
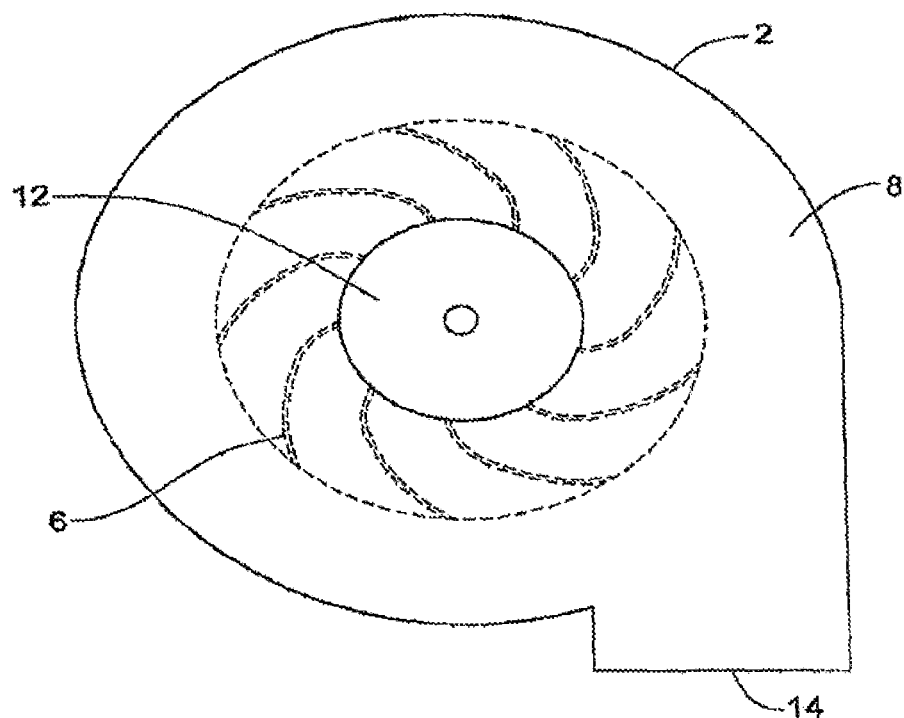
FIG. 1 is a schematic plan view of a blower in accordance with embodiments of the present invention.
Figure 2:
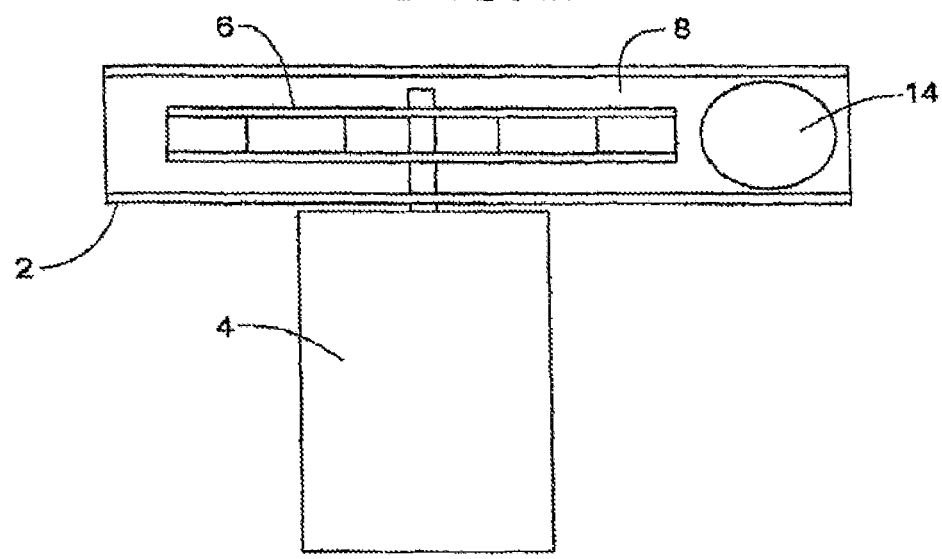
FIG. 2 is a schematic vertical cross-section of a blower in accordance with embodiments of the present invention.

A blower 2 in accordance with embodiments of the present invention is illustrated in FIGS. 1 and 2. The blower 2 includes a motor 4, an impeller 6, a volute 8 and an enclosure 10. The volute 8 includes a blower air inlet 12 through which air enters the blower 2 and a blower air outlet 14 through which air exits the blower 2. The impeller 6 illustrated in FIGS. 1 and 2 generates much of the noise that can be heard when the blower 2 is in use. The noise generated by the impeller 6 is substantially dipole in nature. Specifically, the noise generated at the blower inlet 12 and at the blower outlet 14 are closely correlated but optimally out of phase. In certain embodiments and at certain blower speeds, the noise may be out of phase by approximately 180 degrees, for example 180 degrees plus or minus about 41 degrees, 180 degrees plus or minus about 35 degrees, or 180 degrees plus or minus about 27 degrees. As the phase difference between the noise at the inlet and outlet varies away from 180 degrees, the level of noise cancellation achievable may be affected.

It should also be noted that the noise emitted from the inlet and outlet of the blower 2 is typically in-phase at low frequencies but becomes out-of-phase at higher frequencies.

Figure 3:
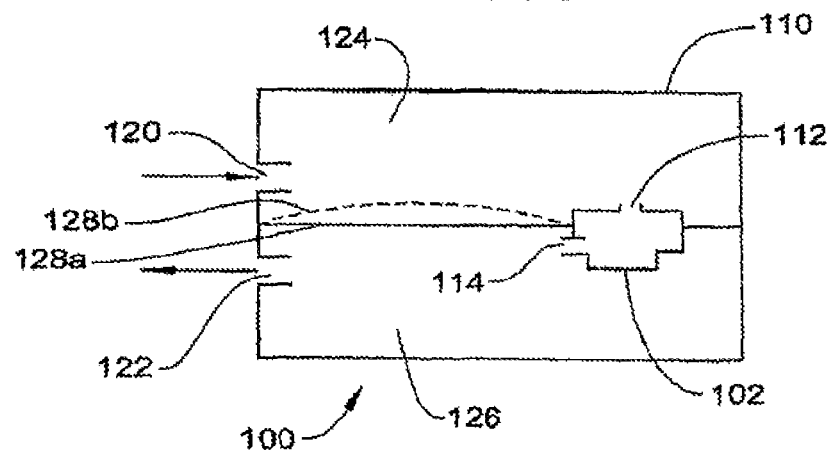
FIG. 3 is a schematic vertical cross-section of an apparatus for reducing the noise generated by a blower in accordance with a first embodiment of the present invention.

FIG. 3 is schematic drawing of an apparatus 100 for reducing the noise generated by blower 102 in accordance with the first embodiment of the present invention. As illustrated in FIG. 3, the blower 102 may be mounted within an enclosure 110 that includes an enclosure air inlet 120 and an enclosure air outlet 122 corresponding to the blower inlet 112 and blower outlet 114. The enclosure 110 is generally divided into an inlet section 124 and an outlet section 126 separated by a flexible membrane 128a-b. The flexible membrane 128a-b is acoustically transparent and allows the sound waves on either side of the membrane 128a-b to add to each other and in some instances, cancel each other out. The flexible membrane 128a-b flexes or deflects as shown in 128b from an unflexed state 128a with the pressure provided by the blower 102 and will be caused to vibrate with the acoustic signal associated with the noise created by the blower 102. The vibration of the membrane 128 thereby achieves at least partial cancellation of the noise generated by the blower 102. The relative internal volumes of the two sections 124 and 126 of the enclosure 110 may be the same or different in order to optimize the cancellation of the noise generated by the blower 102. It is also advantageous to configure the enclosure air inlet 120, enclosure air outlet 122, blower inlet 112 and blower outlet 114 such that the distance between the respective inlets and outlets is the same. This provides better noise cancellation than if the aforesaid distances were different. Of course, in certain embodiments, various system constraints may require that the sizes distances be determined in a manner that does not optimize the cancellation of the noise generated by the blower 102.

Figure 4A:
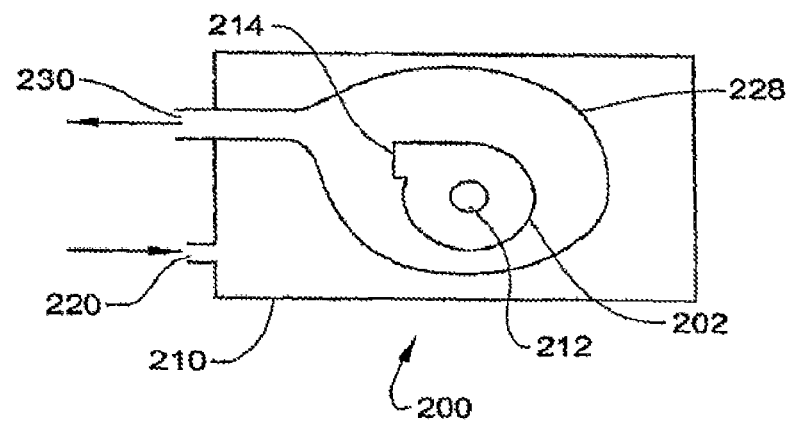
FIG. 4(A) is a schematic horizontal cross-section of an apparatus for reducing the noise generated by a blower in accordance with a second embodiment of the present invention.
Figure 4B:
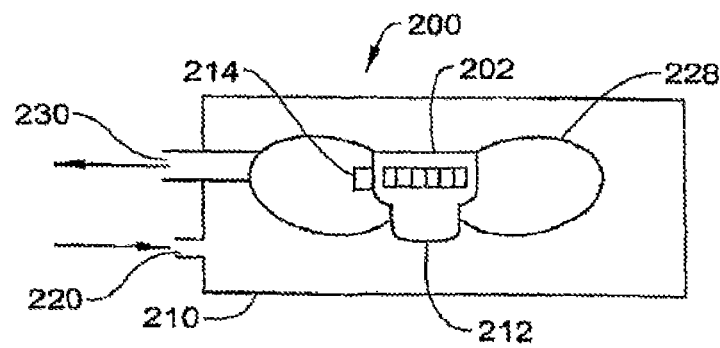
FIG. 4(B) is a schematic vertical cross-section of the apparatus of FIG. 4(A).

FIGS. 4(A) and 4(B) are schematic drawings of an apparatus 200 according to a second embodiment of the present invention for reducing the noise generated by a blower 202. The blower 202 Is surrounded by a donut-shaped flexible membrane 228. In this embodiment, the blower outlet 214 delivers air to the inside of the donut-shaped flexible membrane 22 and there is a passageway 230 from the membrane 228 to outside of the enclosure 210. Accordingly, air enters the enclosure 210 through an enclosure air inlet 220 and is in contact with the outside of the-donut-shaped flexible membrane 228 but is able to flow freely into the inlet 212 of the blower 202 and is blown by the blower 202 into the inside of the donut-shaped flexible membrane 228 and exits the enclosure 210.

This embodiment causes the donut-shaped flexible membrane 228 to expand and the membrane 228 to inflate since the pressure at the blower outlet 214 is higher than the pressure at the blower inlet 212. Once a substantial equilibrium is achieved between the pressure at the blower inlet 212 and the blower outlet 214, the membrane 228 remains in substantial balance and the noise generated by the blower outlet 214 is reduced or cancelled by the noise created at the blower inlet 212 of the blower. It should be understood that equilibrium could, in certain embodiments, mean that the pressures remain constant or, while in other embodiments, could mean that the variations in pressure become regular or sinusoidal.

Figure 5:
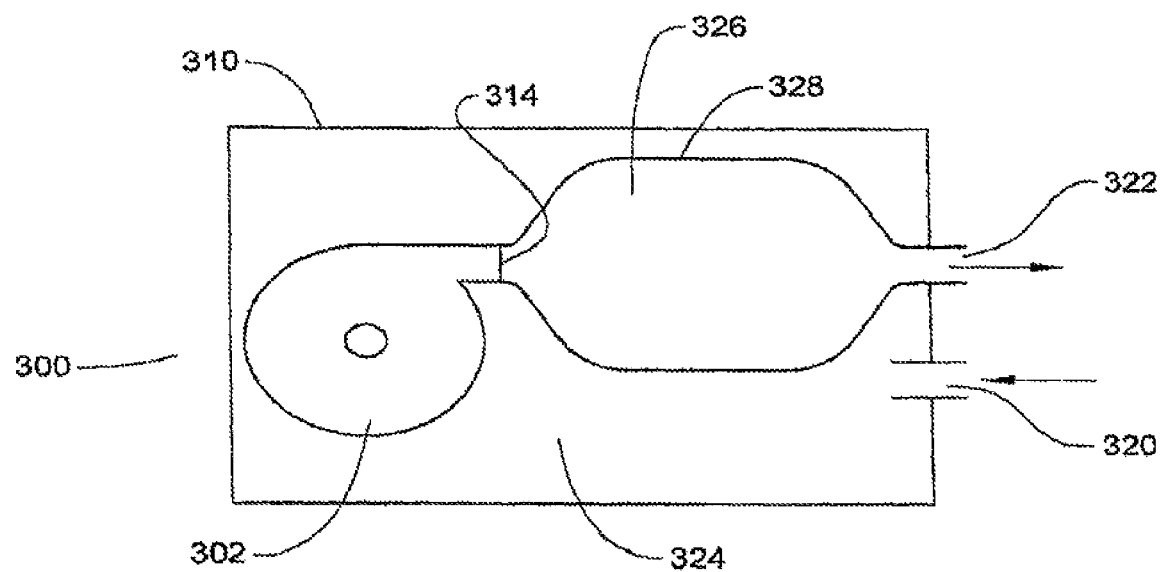
FIG. 5 is a schematic horizontal cross-section of an apparatus for reducing the noise generated by a blower in accordance with a third embodiment of the present invention.

FIG. 5 shows the third embodiment of the present invention which is an apparatus 300 tor reducing the noise generated by the blower 302. The apparatus 300 includes a blower 302 mounted in an enclosure 310 which includes an enclosure air inlet 320 and an enclosure air outlet 322. The blower outlet 314 is coupled to the enclosure air outlet 322 via the flexible membrane 328. In this embodiment, the flexible membrane 328 takes the form of a balloon. The balloon is inflated by the higher blower outlet 314 pressure, for the reasons discussed in relation to FIG. 4. The flexible membrane 328 couples the acoustic signals between the inlet section 324 and the outlet section 326 achieving a reduction in the level of noise.

Figure 6:
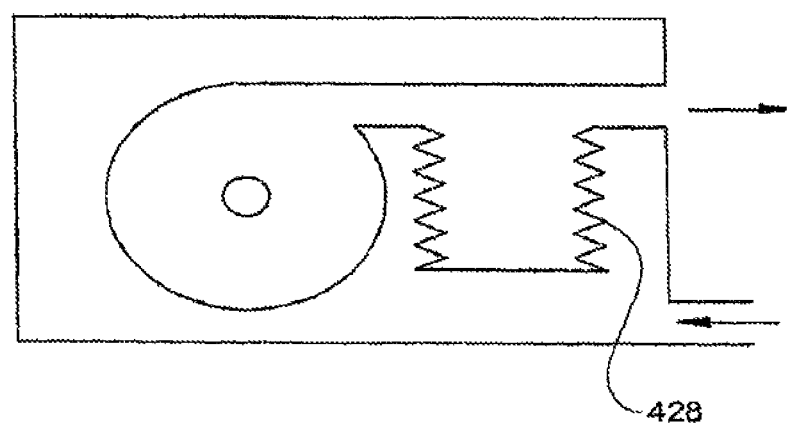
FIG. 6 is a schematic horizontal cross-section of an apparatus for reducing the noise generated by a blower in accordance with a fourth embodiment of the present invention.

FIG. 6 shows the fourth embodiment which is similar to the third embodiment but wherein the flexible membrane 428 takes the form of a bellows 428.

Figure 7:
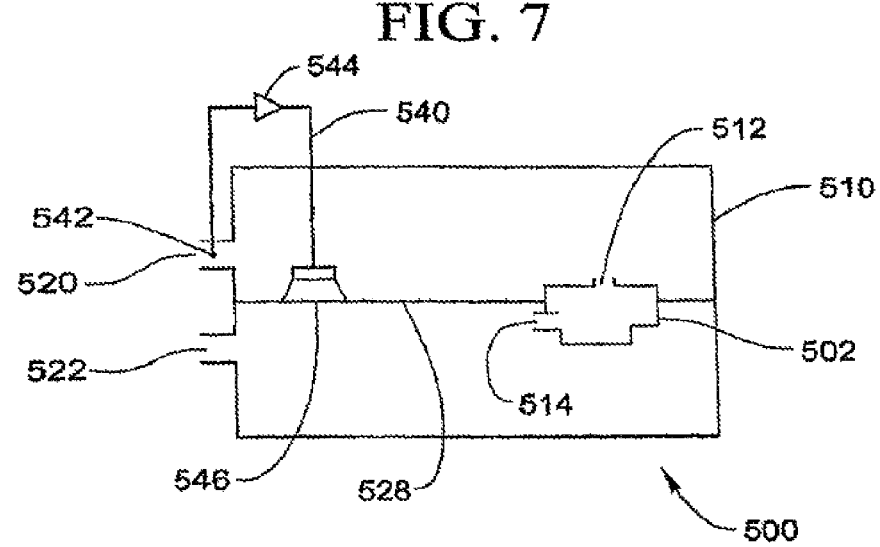
FIG. 7 is a schematic drawing of an apparatus for reducing the noise generated by a blower in accordance with a fifth embodiment of the present invention.

FIG. 7 shows the fifth embodiment which is generally similar to previous embodiments in that it includes blower 502 having inlet 512 and outlet 514 and enclosure 510 having inlet 520 and outlet 522, and membrane 528, but it Includes an active noise reduction system (ANRS) 540 in addition to the passive flexible membrane 528 in its various forms. The ANRS 540 includes a microphone 542 located at or near the enclosure air Inlet 520, an amplifier 544 and a speaker 546. The microphone 542 output signal is transmitted via the amplifier 544 to the speaker 546 which is mounted to or near the flexible membrane 528. In this particular embodiment, the speaker 546 is mounted through the flexible membrane 528 and when the apparatus 500 is operating will emit sound waves which are at least approximately 180 degrees out of phase with the sound waves emitted from the blower air outlet 514. These respective out-of-phase sound waves at least partially cancel each other out resulting in a quieter apparatus 500.

Figure 8A:
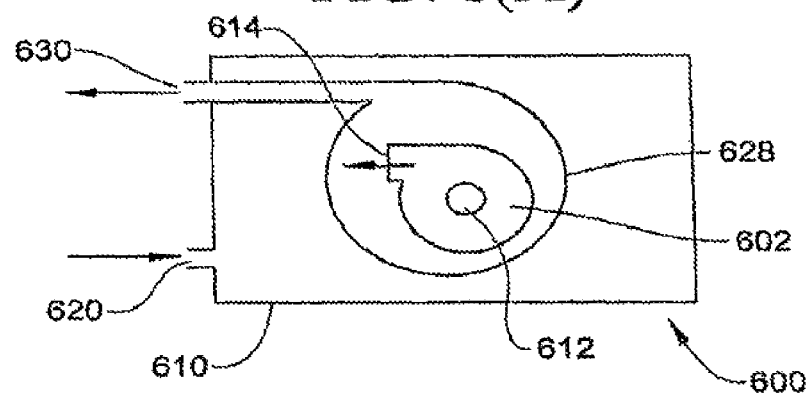
FIG. 8(A) is a schematic horizontal cross-section of an apparatus for reducing the noise generated by a blower in accordance with a sixth embodiment of the present invention.
Figure 8B:
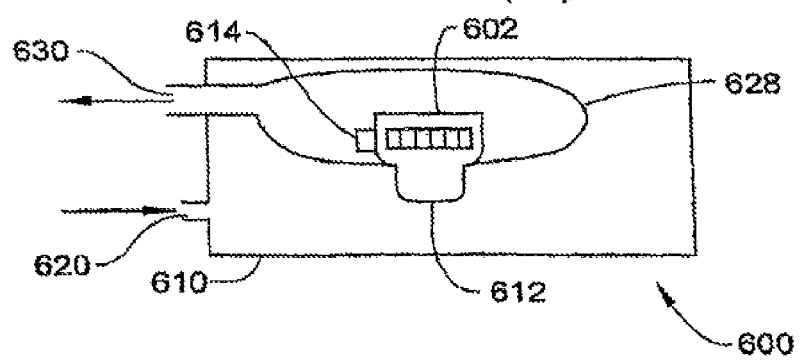
FIG. 8(B) is a schematic vertical cross-section of the apparatus of FIG. 8(A) in accordance with an embodiment of the present invention.

FIG. 8(A) & (B) is a schematic drawing of an apparatus 600 according to a sixth embodiment of the present invention for reducing the noise generated by a blower 602. The blower 602 is surrounded by a flexible membrane 628. In this embodiment, the blower outlet 614 delivers air to the inside of the flexible membrane 628 and there is a passageway 630 from the membrane 628 to outside of the enclosure 610. Accordingly, air enters the enclosure 610 at enclosure air inlet 620 and is in contact with the outside of the flexible membrane 628 but is able to flow freely into the inlet 612 of the blower 602 and is blown by the blower 602 into the inside of the donut shaped flexible membrane 628 and exits the enclosure 610 at the passageway 630. This causes the flexible membrane 628 to inflate since the pressure at the blower outlet 614 is higher than the pressure at the blower Inlet 612. Once a substantial equilibrium is achieved between the pressure at the blower inlet 612 and the blower outlet 614, the membrane 628 remains in substantial balance and the noise generated by the blower outlet 614 is reduced or cancelled by the noise created at the blower inlet 612. It should be understood that equilibrium could, in certain embodiments, mean that the pressures remain constant, while in other embodiments, could mean that the variations in pressure become regular or sinusoidal.

Figure 9:
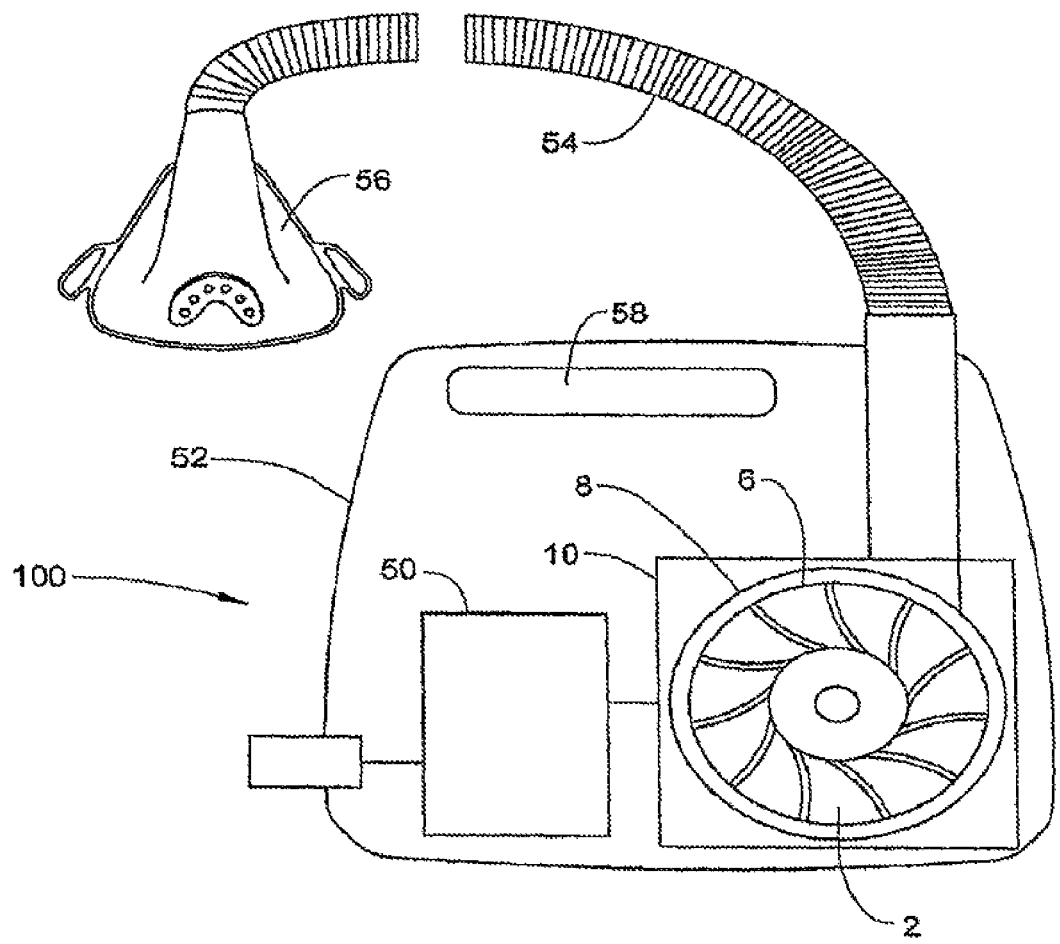
FIG. 9 is a schematic plan view of a respiratory device including a blower in accordance with embodiments of the invention.

FIG. 9 is a schematic plan view of a respiratory device 100 including an apparatus including a blower 2 according to any of the embodiments of the invention, a controller 50, an external housing 52, with a carrying handle 58 for carrying the device 100, an air delivery conduit 54 and a patient interface 56. The blower 2 includes a motor 4, impeller 6, a volute 8 and an enclosure 10 which contains the flexible membrane (not drawn in this Figure). In use, the respiratory device may be turned on and allowed to equilibrate if necessary. The patient interface may be placed on the patient, for example over the nose, or over the mouth and nose, or in the nose depending on the type of interface, and the air can flow from the blower through the delivery conduit to the patient Interface and Into the patient's respiratory system. The controller may be a set point controller and/or may control the air flow using feedback control by measuring any of a number of parameters including, without limitation, outlet pressure, outlet air flowrate, a patient's blood oxygen level via a blood oxygen sensor, a patients respiration rate, or a patients pulse rate, for example by controlling the blower speed or the air inlet or outlet size. The control may be proportional, integral and/or derivative. The device can be used for many different treatments. For example, the device can be used to treat a patient suffering from obstructive sleep apnea, and can be used as a continuous positive air pressure device. The reduced noise of the blower of the device provides for a more successful treatment than other sleep apnea devices as a result of more therapeutic sleep that fs less interrupted by the noise of the respiratory device.

Figure 10A:
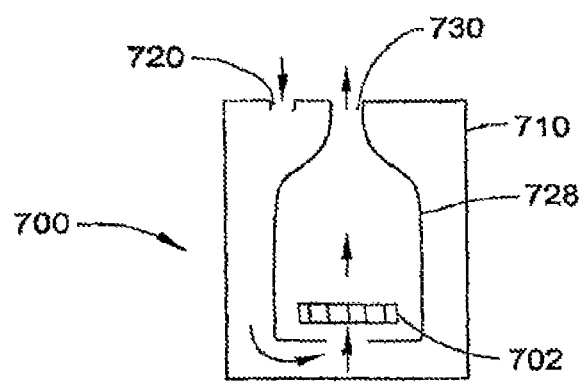
FIG. 10(A) is a schematic cross-section of an apparatus for reducing the noise generated by a blower in accordance with an embodiment of the present invention.
Figure 10B:
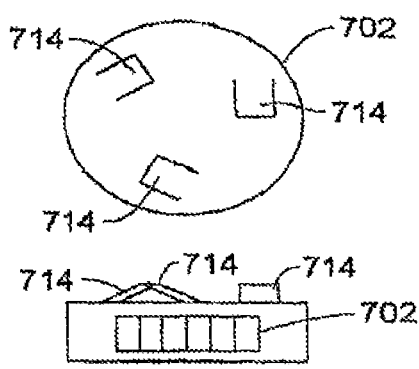
FIG. 10(B) is a schematic cross-section of a blower of the apparatus of FIG. 10(A) in accordance with an embodiment of the present invention.

FIG. 10 (A) & (B) is a schematic drawing of apparatus 700 according to a seventh embodiment of the present invention for reducing the noise generated by a blower 702. The blower 702 has at one side three blower outlets 714 and a flexible membrane 728. In this embodiment, the blower outlets 714 deliver air to the inside of the flexible membrane 728 and there is a passageway 730 from the flexible membrane 728 to outside of an enclosure 710. Accordingly, air enters the enclosure 710 at an enclosure air inlet 720 and is in contact with the outside of the flexible membrane 728 but is able to flow freely into an inlet 712 of the blower 702 and is blown by the blower 702 into the inside of the flexible membrane 728 and exits the enclosure 710 at the passageway 730. The number of blower inlets 712 may greater than 1, for example, 2, 3, 4, 5, or 6 or more and is only limited by the physical constraints of the blower 702 and the blower outlets 714.

Figure 11:
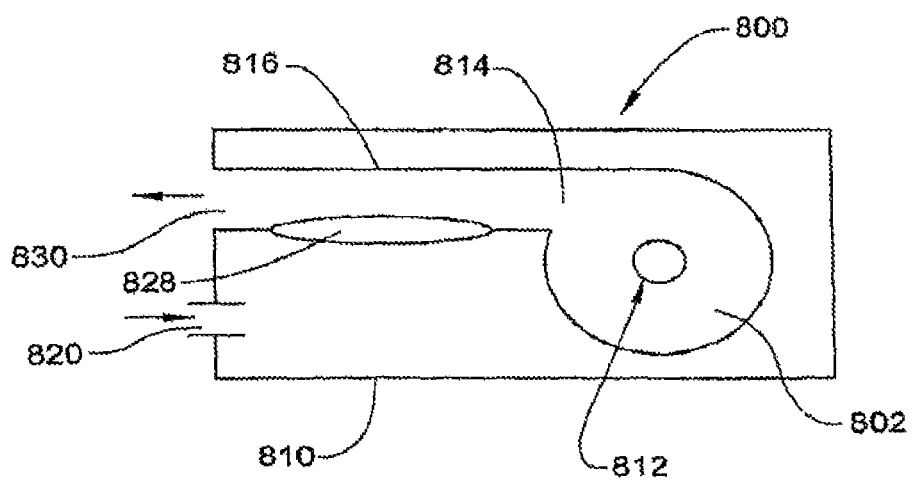
FIG. 11 is a schematic vertical cross-section of an apparatus in accordance with an embodiment of the present invention.

FIG. 11 is a schematic drawing of an apparatus 800 according to an eighth embodiment of the present invention for reducing the noise generated by a blower 802. The blower 802 has a blower outlet conduit 816 connecting blower outlet 814 with enclosure outlet 830. Blower outlet conduit 816 is at least partially comprised along its perimeter and length of flexible membrane. 828. Flexible membrane 828 may take the form of a window in blower outlet conduit 816 having the flexible membrane 828 therein. Accordingly, air enters the enclosure 81o at enclosure inlet port 820 and is in contact with the outside of the flexible membrane 828 but is able to flow freely Into the inlet 812 of the blower 802 and is blown by the blower 802 into thin side of the conduit with a flexible membrane 828 in a "window" and exits the enclosure 810 at port 830.

Figure 12A:
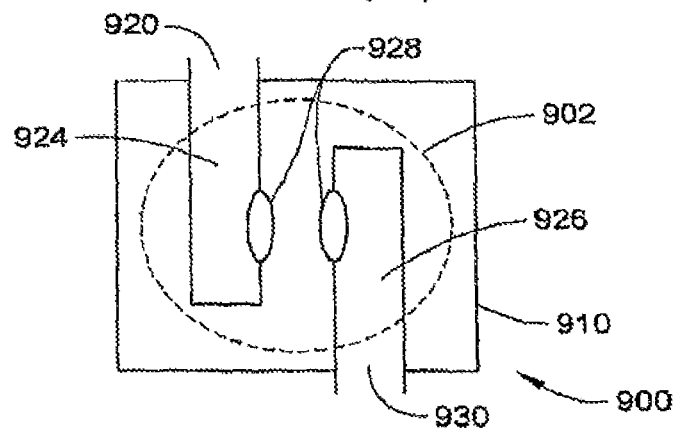
FIG. 12(A) is a schematic cross-section of an apparatus for reducing the noise generated by a blower in accordance with an embodiment of the present invention.
Figure 12B:
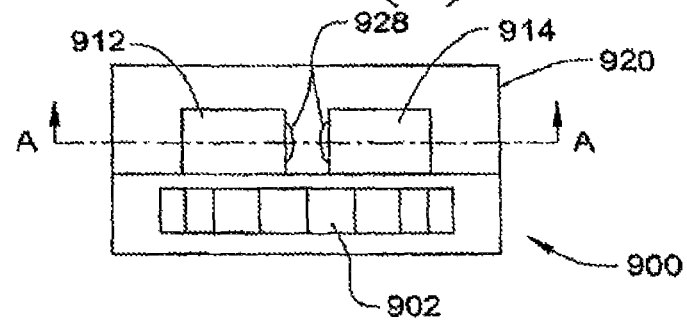
FIG. 12(B) is a schematic cross-section of the apparatus of FIG. 12(A) in accordance with an embodiment of the present invention.

FIG. 12(A) & (B) is a schematic drawing of an apparatus 900 according a ninth embodiment of the present invention for reducing the noise generated by a blower 902. In this embodiment, a blower outlet 914 delivers air to the inside of an outlet conduit 926 comprising a flexible membrane 928 and there is an outlet 930 from the flexible membrane 928 to outside of an enclosure 910. Accordingly, air enters an inlet conduit 924 through an inlet 920, and the air enters the blower 902 through an opening 912. The enclosure 910 comprises ambient air, and the flexible membrane 928 in the inlet conduit 924 and the outlet conduit 926 are in acoustic connection through a layer of ambient air, thereby also canceling out substantial noise. In certain embodiments, the enclosure 910 is a substantially airtight enclosure. In some embodiments, the inlet 920 and the outlet 930 may be on the same side of the enclosure 910 with the conduits 924 and 926 running substantially parallel to each other along their length.

Figure 13:
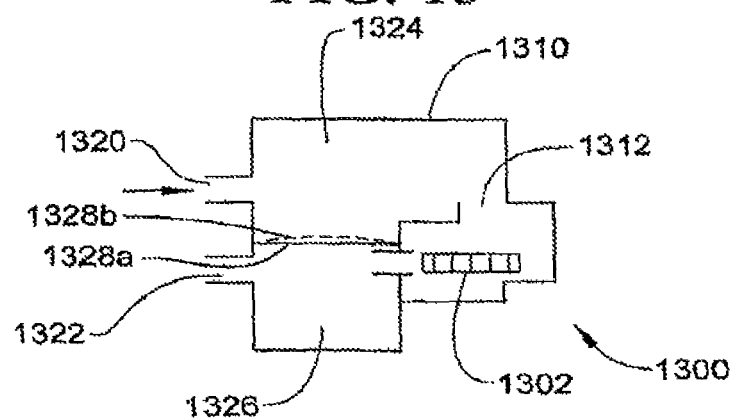
FIG. 13 is a schematic cross-section of an apparatus for reducing the noise generated by a blower in accordance with an embodiment of the present invention.

FIG. 13 is a schematic drawing of an apparatus 1300 for reducing the noise generated by a blower 1302 in accordance with an embodiment of the present invention. As illustrated in FIG. 13, the blower 1302 may 1302 be mounted externally to an enclosure 1310 that includes an enclosure air inlet 1320 and an enclosure air outlet 1322 corresponding to a blower inlet 1312 and a blower outlet 1314, respectively. The enclosure 1310 is generally divided into an inlet section 1324 and an outlet section 1326 separated by a flexible membrane 1328a-b. The flexible membrane 1328a-b is acoustically transparent and allows sound waves on either side of the flexible membrane 1328a-b to add to each other and in some instances, cancel each other out. The flexible membrane 1328a-b flexes as shown in 1328b from an unflexed state 1328a as a result of the pressure provided by the blower 1302 and will be caused to vibrate with the acoustic signal associated with the noise created by the blower 1302. The vibration of the flexible membrane 1328a-b thereby achieves at least partial cancellation of the noise generated by the blower 1302. The relative internal volumes of the two sections 1324, 1326 of the enclosure 1310 may be the same or different in order to optimize the cancellation of the noise generated by the blower 1302. Although this embodiment is shown with a membrane configuration similar to that shown in FIG. 3, other membrane embodiments, including those shown in the FIGURES herein, include external blowers that are part of the present invention, although they are not specifically shown.

Figure 14:
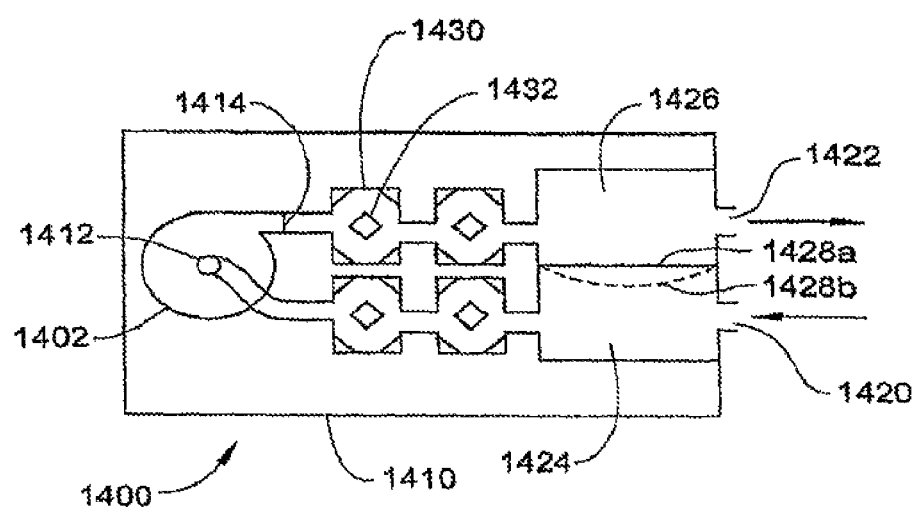
FIG. 14 is a schematic cross-section of an apparatus for reducing the noise generated by a blower in accordance with an embodiment of the present invention.

FIG. 14 is a schematic drawing of an apparatus 1400 for reducing the noise generated by a blower 1402 in accordance with an embodiment of the present invention. The blower 1402 may be mounted to. an enclosure 1410 that includes an enclosure air inlet 1420 and an enclosure air outlet 1422 corresponding to the blower inlet 1412 and blower outlet 1414. The enclosure 1410 is generally divided into an inlet section 1424 and an outlet section 1426 separated by a flexible membrane 1428*a-b*. The flexible membrane 1428*ab* is acoustically transparent and allows sound waves on either side of the membrane 1428*a-b* to add to each other and in some instances, cancel each other out. The flexible membrane 1428*a-b* flexes as shown in 1428*b* from an unflexed state 1428*a* as a result of the pressure provided by the blower 1402 and will be caused to vibrate with the acoustic signal associated with the noise created by the blower 1402. The vibration of the membrane 1428*a-b* thereby achieves at least partial cancellation of the noise generated by the blower 1402.

The relative internal volumes of the two sections 1424, 1426 of the enclosure 1410 may be the same or different in order to optimize the cancellation of the noise generated by the blower 1402. Between inlet section 1424 and the blower, and outlet section 1426 and the blower are four mufflers 1430 (two each between the blower and each section 1424 and 1426). Mufflers 1430 may be used to further reduce noise from the blower using muffling members 1432. Muffling members 1432 may be of any shape, configuration, or composition that serves to muffle the sound, with such parameters known to those of skill in the art. The mufflers 1430 may alternatively be humidifiers that serve to humidify the air while still providing the muffling effect. The humidifiers may also be configured as known to those of skill the relevant art. Though two mufflers 1430 are shown between the inlet section and the outlet section and the blower, it should be understood that any number of mufflers may be used along each flow path and that the number of mufflers need not be equal along each flow path. In addition, it should be understood that mufflers may be placed along both or either flow path before or after the inlet and outlet sections. Furthermore, some embodiments may include multiple noise reduction membrane embodiments. Finally, though this embodiment is shown with a membrane configuration similar to that shown in FIG. 3, other membrane embodiments, including those shown the FIGURES herein, may include mufflers as discussed herein and are part of the present invention, though they. are not specifically shown.

In some embodiments, the distance from the noise source to the noise cancellation membrane or membranes may be sized to maximize noise cancellation. Ideal path lengths are where the time delay in sound traveling from the inlet to the membrane and the outlet to the membrane (i.e. along the inlet and outlet flow paths) is equal or substantially equal. This might commonly means equal distances are best for noise cancellation. Useful path lengths may include differences between the path lengths up to about 5 inches, for example about 4 inches, about 3 inches, about 2 inches, about 1 inch, about 0.5 inches, 0.25 inches, 0.1 inches or even 0.0 inches. Alternatively, the difference in the path lengths may be less than about 0.12 times the shortest wavelength of the sound to be cancelled. For example the difference in the path lengths may be less than 0.1 times, 0.8, 0.6, 0.4, 0.2 or even 0.0 times the wavelength of the sound to be cancelled.

In some embodiments, the distance between the blower inlet and the blower outlet is greater than 20 mm. For example, greater than 30 mm, greater than 35 mm, greater than 40 mm, greater than 50 mm, greater than 60 mm, or greater than 70 mm.

Embodiments of the present invention are useful for reducing or canceling noise at all frequencies detectable by the human ear (approximately 15-20,000 Hz), such as about 20 to about 5000 Hz, about 25 to about 2000 Hz, about 30 to about 1000 Hz, or about 50 to about 500 Hz. Some embodiments are particularly useful for noise reduction or cancellation of sound having relatively low frequencies. For example, such embodiments may reduce noise having frequencies less than 1500 Hz and greater than about 20 Hz, such as frequencies of about 1500 Hz or less, 1250 Hz or less, 1100 Hz or less, 1000 Hz or less, 800 Hz or less, 600 Hz or less, 500 Hz or less, 400 Hz or Jess, 250 Hz or less, 100 Hz or less, 50 Hz or less or even 30 Hz or less. Preferably, the cancelled frequency is 500 Hz or less. For example, some embodiments may be effective reducing noise in frequency ranges of from about 20 to about 1500 Hz, about 50 to about 1000 Hz, about 50 to about 500 Hz, or about 50 to about 200 Hz.

In general, the flexible membranes are as acoustically transparent as possible to maintain integrity at up to about 0.35 cm of water of pressure, while preserving a pressure differential between the enclosure inlets and outlets and result in an acoustic coupling between the inlet and the outlet ports of the blower since the area (e.g., surface area or cross sectional area) of the flexible membrane is much larger than the outlet diameter of the blower. In this situation, there is substantially more acoustic coupling through the flexible membrane than through the inlet and outlet ports of the blower. Accordingly, even smaller flexible membranes may have an, effect on noise reduction, however, in embodiments, it may be preferred to have a flexible membrane with a larger area.

In order to achieve the desired noise reduction the exposed area of the flexible membrane when Inflated generally is between about 3 and about 1000 times the surface area of the outlet area of the blower, for example greater than about 5 times, 10 times, 25 times, 30 times, 50 times, 100 times, 200 times, 300 times, 400 times or greater than about 500 times the surface area of the outlet area of the blower. Preferably the exposed area of the flexible membrane is between about 20 times and about 60 times the outlet area of the blower, such as about 25 times, about 30 times or about 50 times. Generally, the upper limit is based on practical considerations, and may be about 1000 times the surface area or less, or about 500 times or less.

Additionally, the flexible membrane may have varying degrees of compliance (i.e., the ease of moving the membrane). Any membrane material having sufficient flexibility and acceptable acoustical transparency may be used. Acoustic transparency is when a minimum acoustic impedance is provided in an acoustic path. The membrane may be made of a flexible material such as plastic foil or a thin metallic sheet. The required flexibility or compliance is dependant on at least the thickness of the membrane, the pressure, the membrane material, the desired noise cancellation, and the desired acoustical transparency. The membrane material may be any of the known plastics or polymers having the properties discussed herein and may be any elasotmer, for example, polyolefin in nature such as for example polyethylene or polypropylene, or a natural or synthetic rubber. Examples of other membrane materials may include polyurethanes, latexes, polyisoprene latex, and silicones. If higher temperatures are expected, the membrane may be of polyamide material.

In some embodiments, the membrane generally has a thickness of about 0.1 mm or more, preferably about 0.2 mm or more. Generally the thickness will be about 20 mm or less, about 10 mm or less, about 5 mm or less, about 1 mm or less or about 0.5 mm or less. For example, the membrane may have a thickness of about 0.1 to about 10 mm, of about 0.2 to about 5 mm, of about 0.2 to about 1 mm, of about 0.2 to about 0.75 mm, or of about 0.3 to about 0.5 mm.

In some embodiments, the pressure caused by the outlet air may be between about 2-35 cm of water, for example about 5-20 cm of water, 8-15 cm of water, such as less than about 25 cm of water, 20 cm of water, 15 cm of water, 12 cm of water, or 8 cm of water or even 5 cm of water.

In some embodiments, it may be beneficial to have a flexible membrane that is very compliant, as the more compliant a membrane, the better acoustical transparency. However, it can be important to balance the flexibility of the membrane with the requirements of the apparatus to ensure that the expanded/inflated membrane does not restrict the inlet air flow path.

Generally, some embodiments of the membrane may have a tensile strength between about 50 and about 11,000 psi, for example about 100 to about 8000 psi, about 150 to about 6000 psi, about 250 to about 5000 psi, about 500 to about 2500 psi. In addition, some embodiments of the membrane may have a tensile set measured after being held at 100% elongation for 1 minute and then released for 1 minute of less than about 30%, for example, less than about 20%, less than about 15%, less than about 10%, less than about 8%, less than about 5%, less than about 2%, less than about 1% or even about 0%.

Other embodiments of the membrane may have values outside these ranges based on the materials used. For example, some metallic sheet membranes may have different tensile strengths, compliance, thickness, tensile set and other properties, while still being suitable for use In some instances. It is within the knowledge of those of skill in the art to determine the appropriate properties based on at least the parameters identified herein and the desired noise reduction and cancellation.

As apparent from this description, the flexible membrane can have any form, such as for example a part of a flat sheet-like of any form including rectangular and circular, bag-like, donut-like, balloon-like or bellow-like, resulting in a high design flexibility. In addition, in some embodiments, the membrane may comprise a relatively solid or hard central portion having a flexible surround or flexible connection points.

In one embodiment, the inlet section and outlet section are separated substantially by one membrane. As shown in the Figures, the separation may consist of more than about 80% of the flexible membrane, for example about 98%, 95%, 90%, or about 85% of the separation between the inlet and outlet section. It is also possible that as little as about 10% of the separation between the inlet and outlet section is formed by the flexible membrane, the remainder being for example a plastic or metal harder material In general, the separation will consist of about 98%. or less of the flexible membrane, meaning that only the sides of the membrane which are used to connect to the enclosure and to the blower are not flexible. In general, about 5% or more of the separation between the two sections will consist of the membrane. A larger area is generally preferred, for example about 10%, 20%, 30%, 40%, 50%, 60%, about 70% or more of the division.

Blowers typically create noise at between about 20-50 decibels. It is desirable to reduce or cancel as much of this noise as possible. Some embodiments of the present invention may cancel or reduce the noise from about 2 to about 15 decibels, about 3 to about 12 dB, about 3 to about 8 dB, or 3 to about 6 dB, for example a reduction of about 3 dB, 4 dB, 5 dB, 6 dB, 8 dB, 10 dB, or about 12 dB.

In some embodiments, the noise may be reduced in these amounts in specific frequency ranges, for example the noise may be reduced 2 to about 15 decibels, about 3 to about 12 dB, about 3 to about 8 dB, or 3 to about 6 dB, for example a reduction of about 3 dB, 4 dB, 5 dB, 6 dB, 8 dB, 10 dB, or about 12 dB in the frequency ranges of from about 20 to about 1100 Hz, about 30 to about 800 Hz, about 50 to about 500 Hz, or about 50 to about 200 Hz.

In another embodiment, the inlet and outlet section are divided by at least two membranes separated by a layer of fluid medium able to transmit acoustic waves between the inlet and outlet sections. The medium generally is a liquid or gas, and is preferably a gas because of ease of design. The gas may be simple ambient air, but may also be a purer gas like helium or nitrogen gas. Ambient air is a preferred working fluid medium. The thickness of the layer of fluid medium generally will be from about 10 c m to about 0.01 mm, for example less than about 5 cm, less than about 2 cm, less than about 1 cm, less than about 5 mm, or less than about 2 mm. Generally, the thickness of the layer of fluid medium will be about 0.1 mm or more, for example 0.5 mm or more or 1 mm or more.

A more specific embodiment relates to a low noise portable flow generating apparatus, comprising a system for passive noise reduction, the apparatus further comprising a casing and a carrying handle, wherein the system for reducing noise generated by a blower comprises: a blower, comprising a motor, an Impeller, an inlet port, and an outlet port; an enclosure comprising an inlet section including an enclosure inlet port and an outlet section including an enclosure outlet port; and at least one flexible membrane inside the enclosure, forming at least part of the wall or walls of the inlet section and the outlet section and providing acoustic communication between the inlet section and the outlet section.

Figure 15:
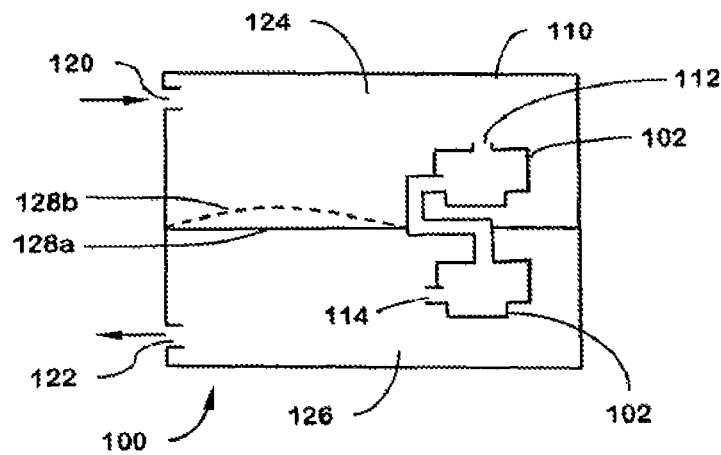
FIG. 15 is a schematic cross-section of an apparatus for reducing the noise generated by a blower in accordance with another embodiment of the present invention.
Figure 16:
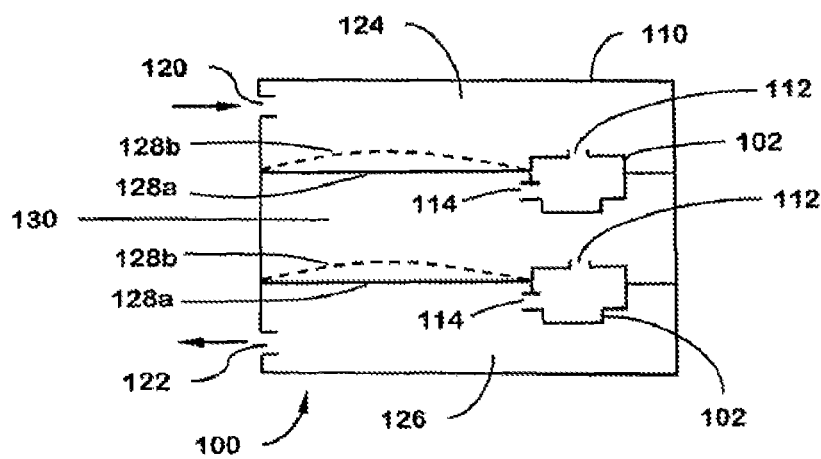
FIG. 16 is a schematic cross-section of an apparatus for reducing the noise generated by a blower in accordance with another embodiment of the present invention.
Figure 17:
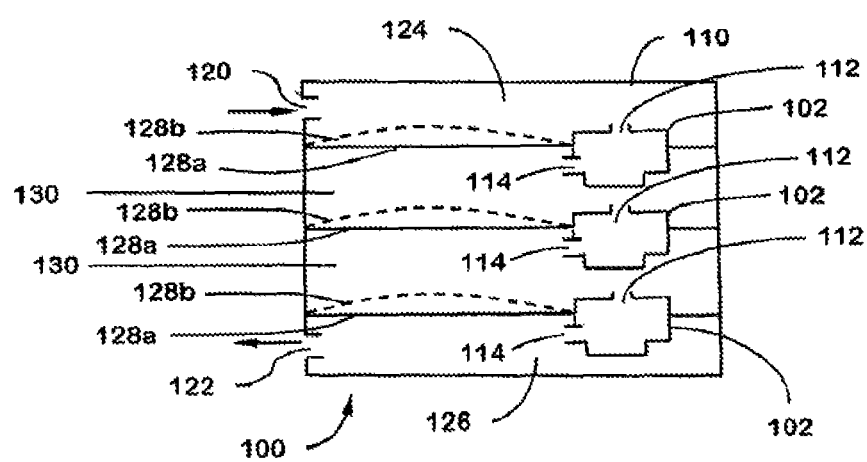
FIG. 17 is a schematic cross-section of an apparatus for reducing the noise generated by a blower in accordance with another embodiment of the present invention.
Figure 18:
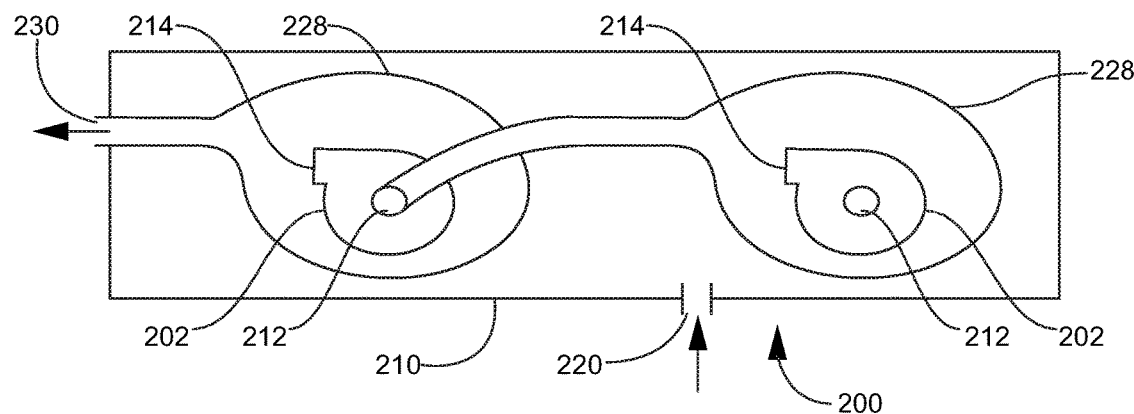
FIG. 18 is a schematic horizontal cross-section of an apparatus for reducing blower noise in accordance with a further embodiment of the present invention.
Figure 19:
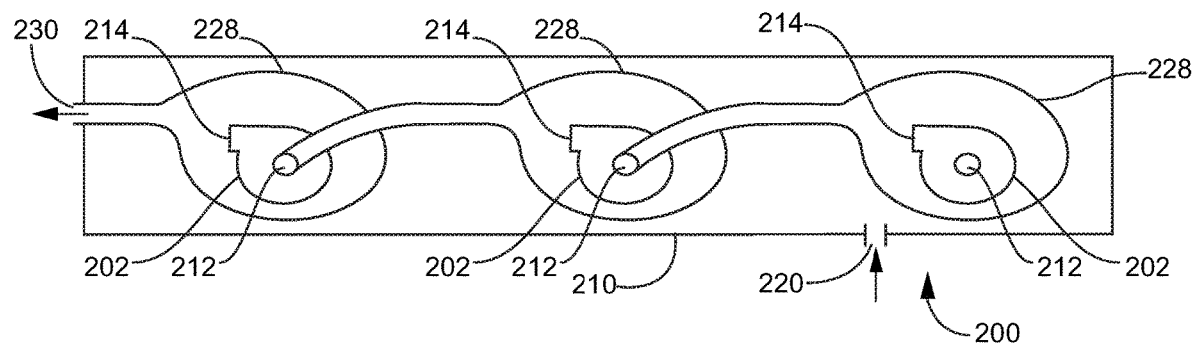
FIG. 19 is a schematic horizontal cross-section of an apparatus for reducing blower noise in accordance with a further embodiment of the present invention.
Figure 20:
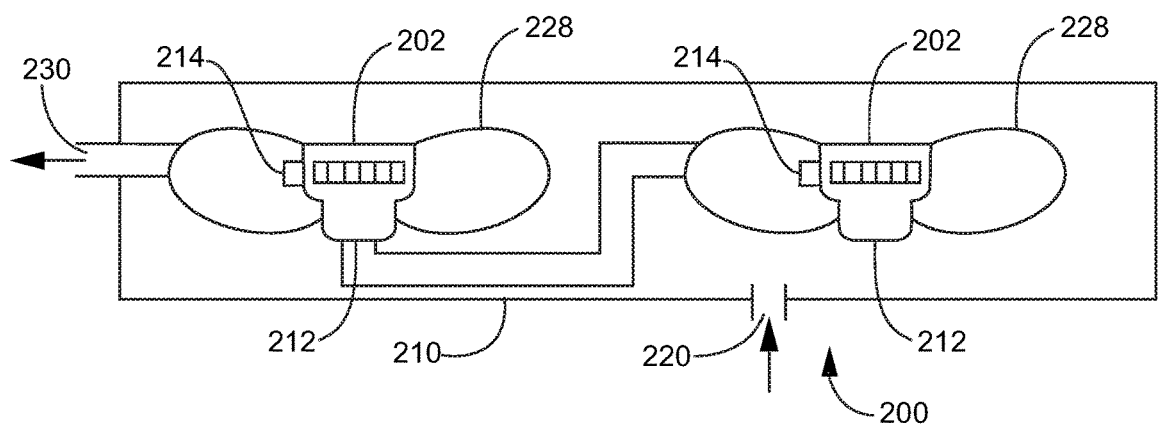
FIG. 20 is a schematic vertical cross-section of an apparatus for reducing blower noise in accordance with a further embodiment of the present invention.
Figure 21:
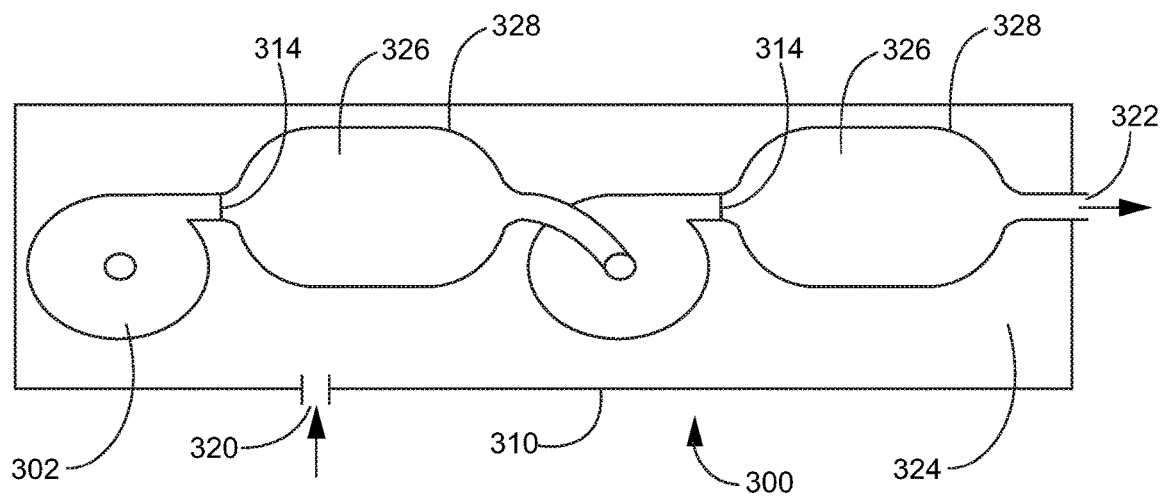
FIG. 21 is a schematic horizontal cross-section of an apparatus for reducing blower noise in accordance with a further embodiment of the present invention.
Figure 22:
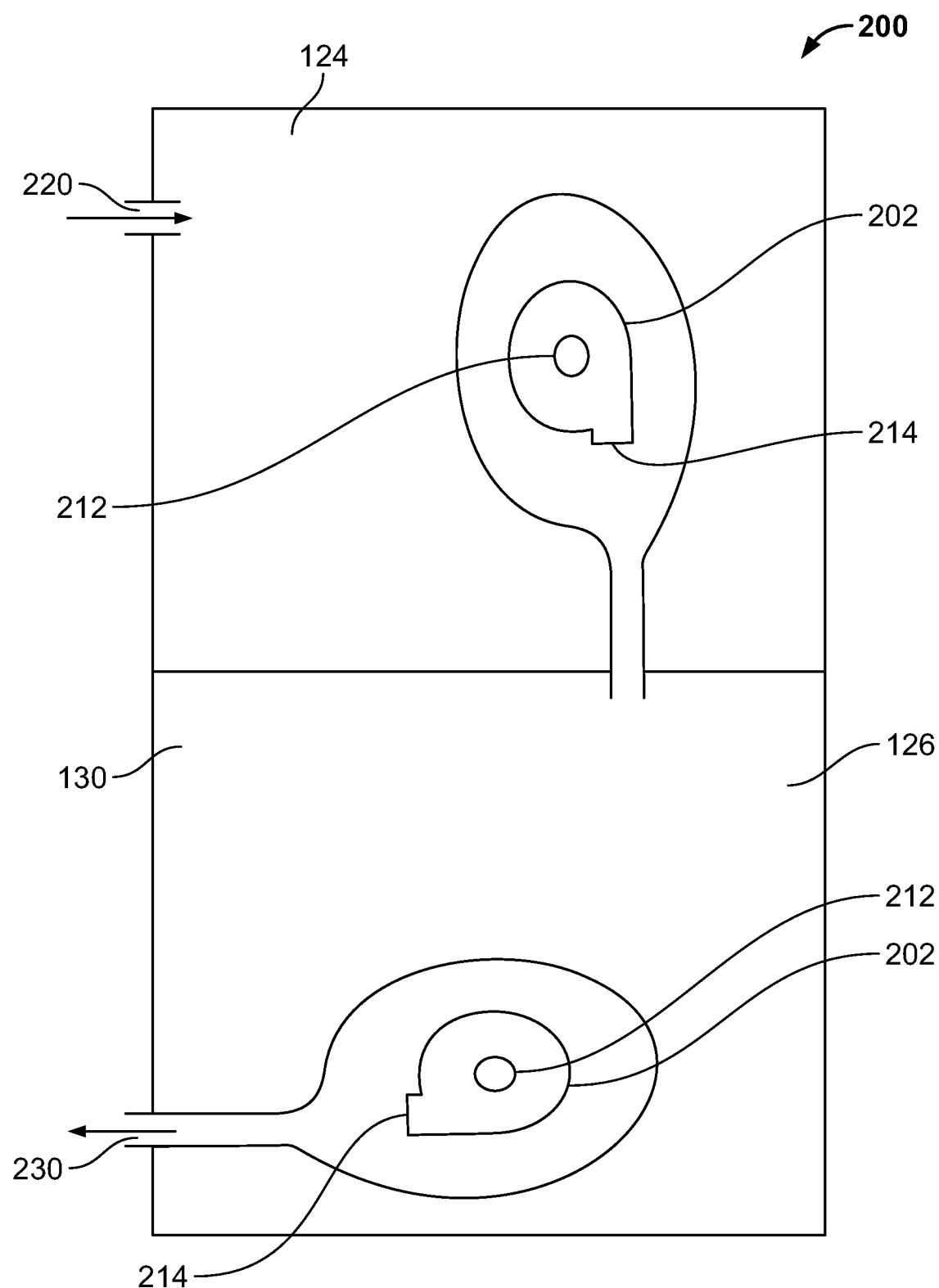
FIG. 22 is a schematic horizontal cross-section of an apparatus for reducing blower noise in accordance with a further embodiment of the present invention.
Figure 23:
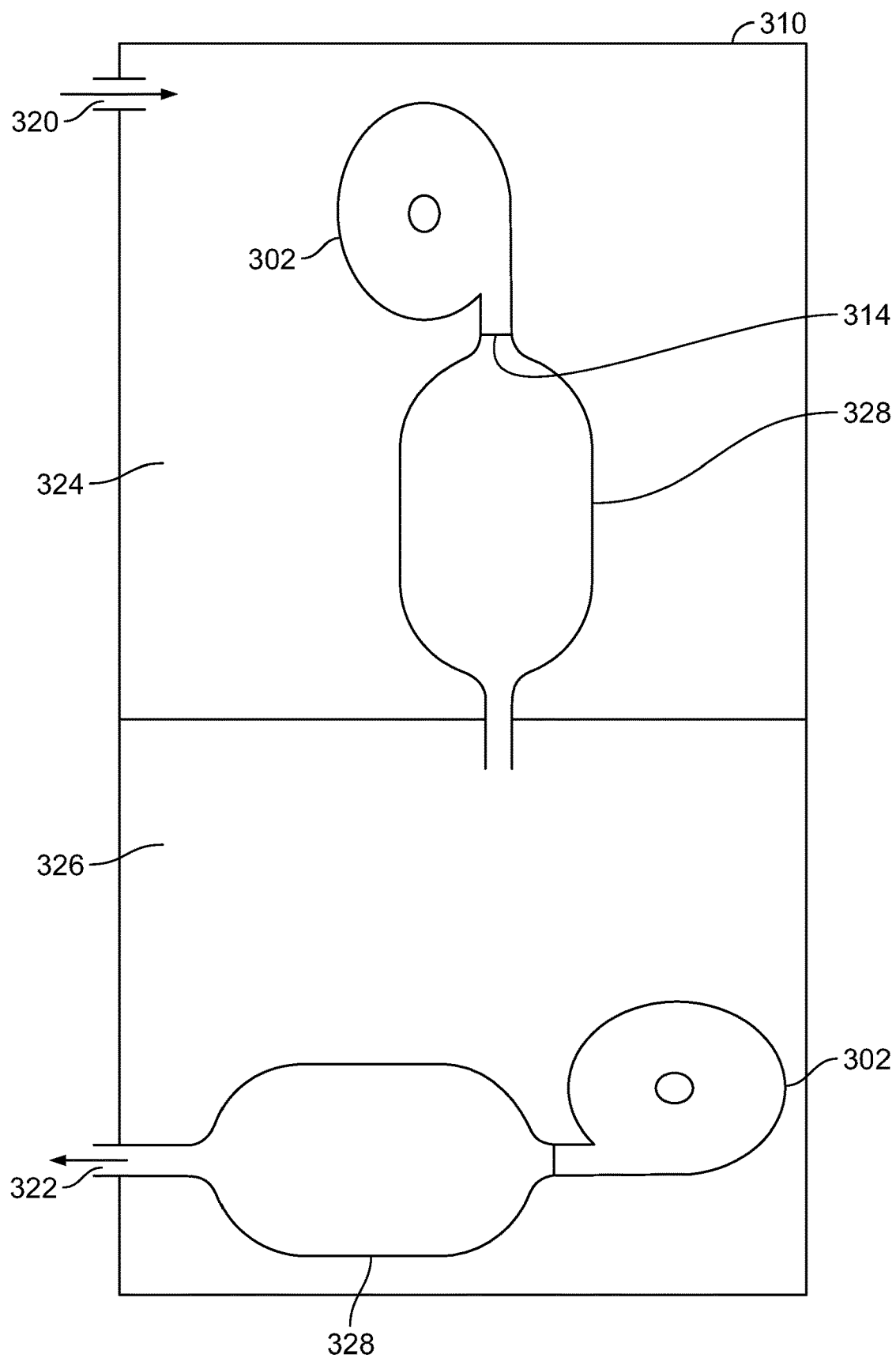
FIG. 23 is a schematic horizontal cross-section of an apparatus for reducing blower noise in accordance with a further embodiment of the present invention.

Another embodiment is adapted for use with a two-stage or three-stage blower (such as the blowers 102 shown in FIGS. 15, 16, and 17) which compresses the incoming air in two (or more) stages via an intermediate region(s) 130. One example of a known two stage blower is disclosed in Resmed's granted U.S. Pat. No. 6,910,483, the entire contents of which is hereby incorporated b y reference. Another exemplary two-stage blower is disclosed in a Resmed U.S. patent application 60/841,202—Resmed reference P237US2 filed on 29 Oct. 2005, the entire contents of which is hereby incorporated by reference. The double-ended blower of P237US2 comprises a blower motor assembly supporting opposed first and second shaft ends, the first and second shaft ends having respective first and second impellers attached thereto and enclose within first and second volutes, respectively, wherein the first volute is connected to an inlet and the second volute is connected to an outlet; and the blower motor assembly supported in a chassis enclosure; a radially outer inter-stage path between the first and second volute, wherein the second volute is at least partially substantially concentrically nested with the radially outer inter-stage gas path.

Two flexible membrane arrangements are envisaged for use with two-stage blowers. In a first arrangement, a flexible membrane is provided allowing acoustic communication between the air entering the first blower stage and the air exiting the second blower stage.

In a second arrangement, noise reduction occurs in two (or more) stages by virtue of two (or more) flexible membranes. A first flexible membrane is provided allowing acoustic communication between the air entering the first blower stage and air exiting the first blower stage into the intermediate region. A second flexible membrane is also provided allowing. acoustic communication between the intermediate region from which air enters the second blower stage and the air exiting the second blower stage Similar membranes are provided for each additional stage where additional stages are used.

It should also be appreciated that the various flexible membrane arrangement provided in embodiments of the invention may be configured so as to provide the sole or primary structural support for the blower 2 and that though the embodiments shown in the FIGURES include one membrane arrangement, the invention includes embodiments that include any number of membrane arrangements. For example some embodiments may include 2 or more membrane arrangements, such as 3 or 4 or more. In general, the enclosure may comprise (n) intermediate sections and (n+1) flexible membranes and each of the (n+1) flexible membranes may be configured to divide the enclosure into the inlet section and the (n) intermediate sections. FIGS. 18-23 show two-stage and three-stage, some with intermediate sections, with the flexible membranes as donut-shaped and balloon-like as shown in FIGS. 4 and 5.

Many alterations and modifications of the present invention will be comprehended by a person skilled in the art after having read the foregoing description. It is to be understood that the particular embodiments shown and described by way of illustration are in no way intended to be considered limiting. Therefore, references to details of particular embodiments are not intended to limit the scope of the claims, which in themselves recite only those features regarded as essential to the invention.

The embodiments described herein are intended to be Illustrative of this invention. As will be recognized by those of ordinary skill in the art, various modifications and changes can be made to these embodiments and such variations and modifications would remain within the spirit and scope of the invention defined in the appended claims and their equivalents. Additional advantages and modifications will readily occur to those of ordinary skill in the art. Therefore, the invention in its broader aspects is not limited to the specific details and representative embodiments shown and described herein.

The invention claimed is:

1. A system for reducing noise generated by a blower, the system comprising:
a blower, comprising a motor, an impeller, a blower inlet, and a blower outlet, wherein the blower inlet is a first distance from the blower outlet;
an enclosure in which the blower is mounted, the enclosure being divided into an inlet section including an enclosure air inlet and an outlet section including an enclosure air outlet, the outlet section having a higher pressure than the inlet section in use, wherein the enclosure air inlet is a second distance from the enclosure air outlet, and the first distance is the same as the second distance; and
a separator formed with a membrane and configured to divide the enclosure into the inlet section and the outlet section and to provide acoustic communication between the inlet section and the outlet section.

2. The system of claim 1, wherein the separator is at least in part flexible.

3. The system of claim 1, wherein the membrane is configured to vibrate to produce at least a partial cancellation of noise generated by the blower.

4. The system of claim 3, wherein an area of the membrane is substantially larger than a cross-sectional area of the blower outlet.

5. The system of claim 1, wherein the membrane comprises foil.

6. The system of claim 1, wherein the membrane comprises any of a plastic, polymer, elastomer or rubber.

7. The system of claim 1, wherein the membrane is metallic.

8. The system of claim 1, wherein the membrane comprises one or more regions of compliance.

9. The system of claim 1, further comprising a layer formed by the membrane and an additional membrane, the layer providing a fluid medium to transmit acoustic waves between the inlet section and the outlet section.

10. The system of claim 1, further comprising a controller for controlling the blower, wherein the blower is configured with the controller to provide an air flow for a respiratory therapy and wherein the system is adapted for coupling with a patient interface.

11. The system of claim 1, wherein the membrane is acoustically transparent and allows sound waves on either side of the membrane to add to each other.

12. A system for reducing noise generated by a blower, the system comprising:
a blower, comprising a motor, one or more impellers, a blower inlet, and a blower outlet, wherein the blower inlet is a first distance from the blower outlet;
an enclosure in which the blower is mounted, the enclosure being divided into (a) an inlet section including an enclosure air inlet, (b) an outlet section including an enclosure air outlet and having a higher pressure than the inlet section when in use, and (c) one or more intermediate sections located between the inlet section and the outlet section, wherein the enclosure air inlet is a second distance from the enclosure air outlet, and the first distance is the same as the second distance; and
one or more separators formed with one or more membranes, the one or more separators each configured to divide the enclosure and to provide acoustic communication between respective two sections out of the inlet section, the outlet section and at least one of the one or more intermediate sections.

13. The system of claim 12, wherein the one or more separators is at least in part flexible.

14. The system of claim 12 wherein the one or more membranes is configured to vibrate to produce at least a partial cancellation of noise generated by the blower.

15. The system of claim 12 wherein the one or more membranes comprises foil.

16. The system of claim 12 wherein the one or more membranes comprises any of a plastic, polymer, elastomer or rubber.

17. The system of claim 12 wherein the one or more membranes is metallic.

18. The system of claim 12 wherein the one or more membranes comprises one or more regions of compliance.

19. The system of claim 12 further comprising a layer formed by the one or more membranes and an additional membrane, the layer providing a fluid medium to transmit acoustic waves between the inlet section and the outlet section.

20. The system of claim 12, further comprising a controller configured to control the blower, wherein the blower is configured with the controller to provide an air flow for a respiratory therapy and wherein the system is adapted for coupling with a patient interface.

21. The system of claim 12, wherein each membrane of the one or more membranes is acoustically transparent and allows sound waves on either side of the membrane to add to each other.

* * * * *